(12) United States Patent
Takeko

(10) Patent No.: US 9,050,580 B2
(45) Date of Patent: Jun. 9, 2015

(54) METHOD FOR PRODUCTION OF MICROCAPSULE

(75) Inventor: Eriko Takeko, Niihama (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 548 days.

(21) Appl. No.: 12/443,016

(22) PCT Filed: Oct. 9, 2007

(86) PCT No.: PCT/JP2007/070039
§ 371 (c)(1),
(2), (4) Date: Apr. 29, 2009

(87) PCT Pub. No.: WO2008/047738
PCT Pub. Date: Apr. 24, 2008

(65) Prior Publication Data
US 2010/0008961 A1    Jan. 14, 2010

(30) Foreign Application Priority Data
Oct. 19, 2006  (JP) .................. 2006-284676

(51) Int. Cl.
*A01N 25/34*   (2006.01)
*B01J 13/02*   (2006.01)
*B01J 13/14*   (2006.01)
*A01N 25/28*   (2006.01)
*C08F 2/26*    (2006.01)
*C08F 2/28*    (2006.01)

(52) U.S. Cl.
CPC ............... *B01J 13/14* (2013.01); *A01N 25/28* (2013.01); *C08F 2/26* (2013.01); *C08F 2/28* (2013.01)

(58) Field of Classification Search
CPC ............. A01N 25/28; C08F 2/28; C08F 2/26; B01J 13/14
USPC ............................................................ 424/408
See application file for complete search history.

(56) References Cited

U.S. PATENT DOCUMENTS 4,680,200 A  *  7/1987  Solc ..................... 427/213.34

FOREIGN PATENT DOCUMENTS

| CA | 2082892 A1 | 5/1993 |
|---|---|---|
| JP | 60058237 A | 4/1985 |
| JP | 62-61633 A | 3/1987 |
| JP | 62-204501 A | 9/1987 |
| JP | 3030833 A | 2/1991 |
| JP | 5-212271 A | 8/1993 |
| JP | 7-31869 A | 2/1995 |
| JP | 2004-196718 A | 7/2004 |
| JP | 2005120365 A | 5/2005 |
| WO | 95/13698 A1 | 5/1995 |

* cited by examiner

*Primary Examiner* — Mina Haghighatian
(74) *Attorney, Agent, or Firm* — Sughrue Mion, PLLC

(57) ABSTRACT

It is possible to perform microencapsulation of a bioactive substance having a solid form at ordinary temperature in a predetermined wall thickness and particle size without the need of dissolving the solid biologically active substance in any solvent by a method for producing a microcapsule, comprising: heating an aqueous dispersion comprising a dispersion stabilizer, an ionic surfactant, the solid biologically active substance, a polymerization initiator and a radical-polymerizable monomer subjected to ultrasonic irradiation. Therefore, the method enables to design a desired particle readily and it is useful for the microencapsulation.

6 Claims, No Drawings

METHOD FOR PRODUCTION OF MICROCAPSULE

TECHNICAL FIELD

The present invention relates to a method for microencapsulating a solid biologically active substance.

BACKGROUND ART

In the fields of pharmaceuticals and pesticides, many methods for microencapsulating a biologically active substance have conventionally been tried in order to enhance potency, reduce toxicity and impart stability (see, e.g., WO 95/13698 and JP-A-2004-196718). In the printing and the paper industries, microencapsulation of pigment and dye has already been put in practical use.

For example, there are some known methods for microencapsulating a solid biologically active substance. Microencapsulation by interfacial polymerization generally requires a solid substance to be dissolved in a specific solvent, and must be designed to produce a suitable formulation for the solid substance according to properties of the solid substance, for example, by selecting an appropriate solvent. Microencapsulation by spray-drying produces a microcapsule having low wall denseness to be difficult to achieve well controlled-release, and often produce some aggregates at the time of the production. The method thus has a problem of difficulty in particle design. Microencapsulation by orifice method or the like has a limitation in production method, and is difficult to produce a microcapsule having small particle size. A microcapsule produced by the method also has a problem that in some cases of use as an aqueous suspension, suspension stability cannot be maintained. Microencapsulation by meltable dispersion process has a limitation of a melting point of a coating material that can be used and a problem of a limited feature of the resultant microcapsule.

DISCLOSURE OF THE INVENTION

The present invention provides a method for microencapsulating a solid biologically active substance that can produce a microcapsule having a desired wall thickness and a desired particle size (particle diameter) without dissolving the solid biologically active substance in a solvent.

That is, the present invention provides a method for producing a microcapsule, comprising: heating an aqueous dispersion containing a dispersion stabilizer, an ionic surfactant, a solid biologically active substance, a polymerization initiator and a radical-polymerizable monomer subjected to ultrasonic irradiation.

The present invention also provides a method for producing a microcapsule, comprising: preparing a mixture solution by dissolving a dispersion stabilizer and an ionic surfactant in water, dispersing a solid biologically active substance in the water, and adding a polymerization initiator and a radical-polymerizable monomer to the water; subjecting the mixture solution to ultrasonic irradiation and stirring; and heating the mixture solution. The present invention also provides a method for producing a microcapsule, comprising: mixing a liquid having an aqueous phase containing a dispersion stabilizer uniformly dissolved therein and a pulverized solid biologically active substance dispersed therein with a liquid prepared by adding a radical-polymerizable monomer containing a polymerization initiator dissolved therein to an aqueous phase containing an ionic surfactant and a dispersion stabilizer, which are uniformly dissolved therein, and subjecting the mixture solution to ultrasonic irradiation and stirring; and heating the mixture solution.

In the present invention, the solid biologically active substance can be any organic or inorganic substance as long as it is solid at an ordinary temperature, i.e., 20° C. Examples of the solid biologically active substance include compounds serving as a medicinal active component such as aspirin, tetracycline hydrochloride, fluorouracil and insulin and compounds serving as a pesticidal active component such as insecticidal compounds, fungicidal compounds, herbicidal compounds, plant growth regulating compounds, insect repellent compounds and insect growth regulating compounds.

Examples of the insecticidal compound and the insect growth regulating compound include pyrethroid compounds such as cyfluthrin, cypermethrin, deltamethrin, fenpropathrin, esfenvalerate, tralomethrin, acrinathrin, bifenthrin, resmethrin and tetramethrin; carbamate compounds such as propoxur, isoprocarb, xylylcarb, metolcarb, XMC, carbaryl, pirimicarb, carbofuran, methomyl, oxamyl, fenoxycarp, alanycarb, metoxadiazone and bendiocarb; organophosphorus compounds such as acephate, phenthoate, vamidothion, trichlorfon, monocrotophos, tetrachlorvinphos, dimethylvinphos, phosalone, chlorpyrifos, chlorpyrifos-methyl, pyridafenthion, quinalphos, methidathion, methamidophos, dimethoate, formothion, azinphos-ethyl, azinphos-methyl and salithion; urea compounds having a chitin synthesis inhibitory activity such as diflubenzuron, chlorfluazuron, lufenuron, hexaflumuron, flufenoxuron, flucycloxuron, cyromazine, diafenthiuron, hexythiazox, novaluron, teflubenzuron, triflumuron, 4-chloro-2-(2-chloro-2-methylpropyl)-5-(6-iodo-3-pyridylmethoxy)pyridazin-3(2H)-one, 1-(2,6-difluorobenzoyl)-3-[2-fluoro-4-(trifluoromethyl)phenyl]urea, 1-(2,6-difluorobenzoyl)-3-[2-fluoro-4-(1,1,2,3,3,3-hexafluoropropoxy)phenyl]urea, 2-tert-butylimino-3-isopropyl-5-phenyl-3,4,5,6-tetrahydro-2H-1,3,5-thiadiazon-4-one and 1-(2,6-difluorobenzoyl)-3-[2-fluoro-4-(1,1,2,2-tetrafluoroethoxy)phenyl]urea; pyrazole compounds such as 5-amino-4-dichlorofluoromethylsulfenyl-1-(2,6-dichloro-4-trifluoromethylphenyl) pyrazole and 5-amino-1-(2,6-dichloro-4-trifluoromethylphenyl)-4-trifluoromethylsulfenylpyrazole; chloronicotinyl compounds such as imidacloprid, acetamiprid, nitenpyram, diacloden and clothianidin; macrolide compounds such as spinosad; and others such as cartap, buprofezin, thiocyclam, bensultap, fenoxycarb, fenazaquin, fenpyroximate, pyridaben, pyriproxyfen, hydramethylnon, thiodicarb, chlorfenapyr, fenpyroximate, pymetrozine, pyrimidifen, tebufenozide, tebufenpyrad, triazamate, indoxacarb, sulfluramide, milbemectin, avermectin, clofentezine, boric acid and para-dichlorobenzene.

Examples of the fungicidal compound include benzimidazole compounds such as benomyl, carbendazim, thiabendazole and thiophanate-methyl; phenylcarbamate compounds such as diethofencarb; dithiocarbamate compounds such as thiuram; dicarboximide compounds such as procymidone, iprodione and vinclozolin; azole compounds such as diniconazole, epoxyconazole, tebuconazole, difenoconazole, cyproconazole, flusilazole, triadimefon and hexaconazole; acylalanine compounds such as metalaxyl; carboxyamide compounds such as furametpyr, mepronil, flutolanil and thifluzamide; organophosphorus compounds such as tolclofos-methyl, fosetyl-aluminium and pyrazophos; anilinopyrimidine compounds such as pyrimethanil, mepanipyrim and cyprodinil; cyanopyrrole compounds such as fludioxonil and fenpiclonil; antibiotics such as Blasticidin S, kasugamicin, polyoxin, validamicin and mildiomycin; methoxyacrylate compounds such as azoxystrobin, kresoxim-methyl and metominostrobin; and others such as oxadixyl, PCNB, hydroxyisoxazole, dazomet, dimethirimol, diclomezine, triazine, isoprothiolane, diclocymet, carpropamid, chlorothalonil, manzeb, captan, folpet, oxine-copper, basic copper chloride, tricyclazole, pyroquilon, probenazole, fthalide, cymoxanil, dimethomorph, S-methylbenzo[1.2.3]thiadiazole-7-carbothioate, famoxadone, oxolinic acid, fluazinam, ferimzone, chlobenthiazone, isovaledione, tetrachloroisophthalonitrile, thiophthalimide, oxybisphenoxarsine, 3-iodo-2-propylbutyl carbamate, silver zeolite, silver-silica gel, silver zirconium phosphate, parahydroxybenzoate esters, sodium dehydroacetate and potassium sorbate.

Examples of the herbicidal compound include triazine compounds such as atrazine and metribuzin; urea compounds such as fluometuron, isoproturon and dymron; hydroxybenzonitrile compounds such as bromoxynil and ioxynil; 2,6-dinitroaniline compounds such as pendimethalin and trifluralin; aryloxyalkanoic acid compounds such as 2,4-D, dicamba, fluoroxypyr and mecoprop; sulfonylurea compounds such as bensulfuron-methyl, metsulfuron-methyl, nicosulfuron, primisulfuron-methyl, cyclosulfamuron, imazosulfuron and 1-(2-chloro-6-propylimidazo[1,2-b]pyridazine-3-ylsulfonyl)-3-(4,6-dimethoxy-pyrimidin-2-yl) urea; imidazolinone compounds such as imazapyr, imazaquin and imazethapyr; and others such as bispyribac-sodium, bisthiobac-sodium, acifluofen-sodium, sulfentrazone, paraquat, flumetsulam, triflusulfuron-methyl, fenoxaprop-p-ethyl, cyhalofop-butyl, diflufenican, norflurazone, isoxaflutole, glufosinate-ammonium, glyphosate, bentazon, benthiocarb, mefenacet, propanyl, flutiamide, simetryn, fentrazamide, etobenzanide, swep, oxaziclomefone, oxadiazolone, pyrazolate, prodiamine, cafenstrole, pentoxazone, chlomeprop, pyriftalid, benzobicyclon, bromobutide and pyraclonil.

Examples of the plant growth regulating compound include maleic hydrazide, clormequat, ethephon, gibberellin, mepiquat chloride, thidiazuron, inabenfide, paclobutrazol and uniconazole.

Examples of the insect repellent compounds include 1S,3R,4R,6R-carane-3,4-diol and dipropyl 2,5-pyridinedicarboxylate.

In the present invention, the dispersion stabilizer includes a substance having protective colloid-forming properties. Specific examples of the substance include a polyvinyl alcohol; cellulose derivatives such as hydroxypropylcellulose, hydroxypropylmethylcellulose, hydroxypropylmethylcellulose phthalate, methylcellulose and ethylcellulose; polyalkylene glycols such as polyethylene glycol and polypropylene glycol; starch; and mixtures thereof.

In the present invention, examples of the ionic surfactant include anionic, cationic and amphoteric surfactants.

Examples of the anionic surfactant include salts of sulfuric acid ester, sulfonic acid, carboxylic acid and phosphoric acid ester.

Specific examples of the salt of sulfuric acid ester include salts of alkylsulfuric acid ester, polyoxyethylene alkyl ether sulfuric acid, polyoxyethylene alkylphenyl ether sulfuric acid, polyoxyethylene benzylphenyl ether sulfuric acid, polyoxyethylene styrylphenyl ether sulfuric acid, polyoxyethylene benzylphenyl phenyl ether sulfuric acid, polyoxyethylene styrylphenyl phenyl ether sulfuric acid and polyoxyethylene polyoxypropylene sulfuric acid ester.

Specific examples of the salt of sulfonic acid include salts of paraffinsulfonic acid, sulfosuccinic acid dialkyl ester, sulfosuccinic acid alkyl ester, alkylarylsulfonic acid, dialkylarylsulfonic acid, alkylarylsulfonic acid-formalin condensate, arylsulfonic acid-formalin condensate, alkyldiphenyl ether disulfonic acid, ligninsulfonic acid, polyoxyethylene alkyl phenyl ether sulfonic acid, alkenylsulfonic acid and polyoxyethylene alkyl ether sulfosuccinic acid half-ester.

Specific examples of the salt of carboxylic acid include salts of higher fatty acid, fatty acid sarcosinate, methacrylic acid polymer, acrylic acid-methacrylic acid copolymer, acrylic acid-methacrylic acid polyoxyethylene ester copolymer, acrylic acid-methyl acrylate copolymer, acrylic acid-vinyl acetate copolymer, acrylic acid-maleic acid copolymer, maleic acid-isobutylene copolymer and styrene-maleic acid copolymer.

Specific examples of the salt of phosphoric acid ester include salts of polyoxyethylene alkyl ether phosphoric acid, polyoxyethylene monoalkyl phenyl ether phosphoric acid, polyoxyethylene dialkyl phenyl ether phosphoric acid, polyoxyethylene benzylphenyl ether phosphoric acid, polyoxyethylene benzylphenyl phenyl ether phosphoric acid, polyoxyethylene styrylphenyl ether phosphoric acid, polyoxyethylene styrylphenyl phenyl ether phosphoric acid, polyoxyethylene polyoxypropylene phosphoric acid ester and alkylphosphoric acid ester. Examples of the salt include sodium, potassium, ammonium, alkanolamine, calcium and magnesium salts.

Examples of the cationic surfactant include alkylamine hydrochlorides such as dodecylamine hydrochloride; alkyl quaternary ammonium salts such as dodecyltrimethylammonium, alkyldimethylbenzylammonium, alkylpyridinium, alkylisoquinolinium and dialkylmorphorinium salts; and others such as benzethonium chloride and polyalkylvinylpyridinium. Examples of the salt include chloride, bromide, methylsulfate and ethylsulfate.

Examples of the amphoteric surfactant include N-laurylalanine, N,N,N-trimethylaminopropionic acid, N,N,N-trihydroxyethylaminopropionic acid, N-hexyl-N,N-dimethylaminoacetic acid, 1-(2-carboxyethyl)pyridinium betaine and lecithin.

In the present invention, the polymerization initiator includes a thermal polymerization initiator soluble in the radical-polymerizable monomer described below.

Examples of the thermal polymerization initiator include azo compounds such as 2,2'-azobisisobutyronitrile, 2,2'-azobis(2-methylbutyronitrile), 1,1'-azobis(cyclohexane-1-carbonitrile), 2,2'-azobis(2,4-dimethylvaleronitrile), 2,2'-azobis(2,4-dimethyl-4-methoxylvaleronitrile), dimethyl-2,2'-azobis(2-methylpropionate) and 2,2'-azobis(2-hydroxymethylpropionitrile); organic peroxides such as lauryl peroxide, tert-butyl hydroperoxide, benzoyl peroxide, tert-butyl peroxybenzoate, cumene hydroperoxide, diisopropyl peroxycarbonate, di-n-propyl peroxycarbonate, tert-butyl peroxyneodecanoate, tert-butyl peroxypivalate and 3,5,5-trimethylhexanoyl peroxide; and inorganic peroxides such as potassium persulfate, ammonium persulfate and hydrogen peroxide. A redox-based initiator using the thermal polymerization initiator in combination with a reductant may also be used as the polymerization initiator.

In the present invention, an amount of the polymerization initiator used is not specifically limited, but generally 0.01 to 10 parts by weight, and preferably 0.1 to 5 parts by weight based on 100 parts by weight of the radical-polymerizable monomer.

In the present invention, examples of the radical-polymerizable monomer include styrene-, α-methylstyrene, α-methoxystyrene, m-bromostyrene, m-chlorostyrene, o-bromostyrene, o-chlorostyrene, p-bromostyrene, p-chlorostyrene, p-methylstyrene, p-methoxystyrene, 2-vinylpyridine, isobutene, 3-methyl-1-butene, butyl vinyl ether, methyl vinyl ketone, nitroethylene, vinylidene cyanide, ethylene, propylene, vinyl chloride, vinyl acetate, acrolein, methylacrolein, acrylamide, N-methylolacrylamide, N,N-dimethylacrylamide, diacetoneacrylamide, N-octadecylacrylamide, ethyl α-acetoxyacrylate, ethyl α-chloroacrylate, methyl α-chloroacrylate, methyl α-cyanoacrylate, methyl α-phenylacrylate, benzyl acrylate, butyl acrylate, ethyl acrylate, 2-ethylhexyl acrylate, stearyl acrylate, lauryl acrylate, tridecyl acrylate, 2-hydroxyethyl acrylate, 2-hydroxypropyl acrylate, 2-methoxyethyl acrylate, 2-butoxyethyl acrylate, ethoxyethoxyethyl acrylate, methyl triglycol acrylate, cyclohexyl acrylate, tetrahydrofurfuryl acrylate, cyanoethyl acrylate, ferrocenylmethyl acrylate, glycidyl acrylate, heptafluorobutyl acrylate, methyl acrylate, octyl acrylate, methyl trifluoroacrylate, 2-chloroethyl acrylate, 2-nitrobutyl acrylate, acrylic acid, α-bromoacrylic acid, 2-hydroxyethylacryloylphosphate, acrylonitrile, allyl glycidyl ether, allylacetic acid, allyl alcohol, allylbenzene, N-allylstearylamide, 1-butene, 2-butene, N-vinylcaprolactam, ethyl N-vinylcarbamate, N-vinylcarbazole, crotonaldehyde, crotonic acid, 1,1-diphenylethylene, tetrafluoroethylene, diethyl fumarate, 1-hexene, 1-vinylimidazole, 1-vinyl-2-methylimidazole, indene, diethyl maleate, maleic anhydride, maleimide, methacrylamide, benzyl methacrylate, butyl methacrylate, ethyl methacrylate, ferrocenyl methyl methacrylate, glycidyl methacrylate, isopropyl methacrylate, propyl methacrylate, n-butyl methacrylate, isobutyl methacrylate, sec-butyl methacrylate, t-butyl methacrylate, 2-ethylhexyl methacrylate, cyclohexyl methacrylate, isodecyl methacrylate, lauryl methacrylate, tridecyl methacrylate, stearyl methacrylate, methyl methacrylate, phenyl methacrylate, 2-hydroxyethyl methacrylate, 2-hydroxypropyl methacrylate, 2-ethoxyethyl methacrylate, tetrahydrofurfuryl methacrylate, dimethylaminoethyl methacrylate, diethylaminoethyl methacrylate, 3-chloro-2-hydroxypropyl methacrylate, methacrylic acid, methacryloxyethyl phosphate, polyethylene glycol monomethacrylate, polypropylene glycol monomethacrylate, N-methylolmethacrylamide, methacrylonitrile, methacryloylacetone, 2-isopropenyl-2-oxazoline, 2-vinylquinoline, vinyl benzoate, vinyl dodecyl ether, vinyl ethyl sulfoxide, vinyl formate, vinyl isobutyl ether, vinyl laurate, vinyl phenyl ether, acetylene and phenylacetylene.

In the present invention, an amount of the radical-polymerizable monomer used is not specifically limited, but generally 0.01 to 70% by weight, and preferably 0.1 to 50% by weight in the mixture to be subjected to ultrasonic irradiation.

The method for producing a microcapsule will be more specifically described in detail below.

An aqueous mixture comprising the solid biologically active substance, the dispersion stabilizer, the ionic surfactant, the polymerization initiator and the radical-polymerizable monomer is prepared. The mixture can be generally prepared by uniformly dissolving the dispersion stabilizer and the ionic surfactant in the aqueous phase, dispersing the pulverized solid bioactive substance in the aqueous phase and adding the radical-polymerizable monomer containing the polymerization initiator dissolved therein to the aqueous phase. The operation of mixing is not necessarily performed in this order. For example, the dispersion stabilizer, the ionic surfactant and the pulverized solid biologically active substance may be mixed at first, or the polymerization initiator may be added to the aqueous phase separately from the radical-polymerizable monomer. In the case of using an oil-soluble polymerization initiator, it is preferably dissolved in the radical-polymerizable monomer before addition to the aqueous phase.

The prepared mixture is subjected to ultrasonic irradiation and stirred. In this time, a homogenizer equipped with an ultrasonic irradiation device is generally used. Various homogenizer equipped with an ultrasonic irradiation device are commercially available, including Ultrasonic Disruptor UD-201 (Tomy Seiko Co., Ltd.), Ultrasonic Homogenizer (Nissei Corporation.), GSD150CVP, GSD300CVP, GSD600CVP, GSD1200CVP, GSD300RCVP, GSD600RCVP, GSD600RCVP-B, GSD1200RCVP (Ginsen Co., Ltd.), SONIFIER (Branson Japan), SPC, 150VT, 300VT (Shinka Industry Co., Ltd.), Ultrasonic Homogenizer Model 150V/T, 300V/T, Ultrasonic 3000 (Biologics, Inc.), USP 200S Ultrasonic Homogenizer (IKA), Omni Ruptor 400 Ultrasonic Homogenizer (Omni International), Misonix (SPI Supplies and Structure Probe, Inc.), for example. Ultrasonic irradiation is performed to reduce a volume median diameter of the radical-polymerizable monomer to 2 μm or less. A period of ultrasonic irradiation is thus preferably sufficiently long to do so. The period is generally about 1 minute to 30 minutes.

In the mixture subjected to ultrasonic irradiation, additional stirring will result in finely-divided radical-polymerizable monomer sufficiently adsorbed on around the solid biologically active substance. Stirring is thus preferably continued for about 30 minutes to 5 hours.

It is also possible to mix a liquid having an aqueous phase containing the dispersion stabilizer uniformly dissolved therein and the pulverized solid biologically active substance dispersed therein with a liquid prepared by uniformly dissolving the ionic surfactant and the dispersion stabilizer in an aqueous phase, adding the radical-polymerizable monomer containing a polymerization initiator dissolved therein to the aqueous phase, and subjecting to ultrasonic irradiation.

The mixture is then heated and gently stirred to give microcapsules. A temperature is not lower than a reaction temperature of the polymerization initiator, and is generally 25 to 85° C. During gently stirring, the finely-divided radical-polymerizable monomer adsorbed on the solid biologically active substance generally polymerizes to form a wall encompassing the solid biologically active substance. A period of stirring is generally within the range of 1 to 90 hours.

The ionic surfactant is generally contained in the mixture in the concentration lower than a concentration at which the ionic surfactant can form a micelle, or a critical micelle concentration, in order to avoid emulsion polymerization in the aqueous phase. As used herein, the critical micelle concentration refers a concentration above which molecules of a surfactant start aggregating into colloidal aggregates referred to as micelles, and is inherent in the surfactant.

The present invention also provides a microcapsule composition comprising the solid biologically active substance microencapsulated with a polymer derived from the radical-polymerizable monomer subjected to ultrasonic irradiation, the dispersion stabilizer and the ionic surfactant that are dispersed in water. The microcapsule composition can be produced by the method for producing a microcapsule described above.

The microcapsule composition of the present invention comprises generally 0.01 to 70% by weight, and preferably 0.1 to 50% by weight of the solid bioactive substance, generally 0.001 to 10% by weight, and preferably 0.005 to 5% by weight of the dispersion stabilizer, and generally 0.001 to 5% by weight, and preferably 0.005 to 1% by weight of the ionic surfactant.

In the microcapsule composition of the present invention, a volume median diameter of the solid biologically active substance is generally 0.1 to 100 μm, and preferably 0.2 to 50 μm. A volume median diameter can be measured with, for example, Mastersizer 2000 (Malvern Instruments Ltd), SALD-2200 (Shimadzu Corporation), Microtrac MT3000 (Nikkiso Co., Ltd.).

The microcapsule composition of the present invention may be an aqueous dispersion of the microcapsule as prepared by the method of microencapsulation, or an aqueous dispersion prepared by adding a thickener, a preservative, an antifreezing agent, a specific-gravity control agent and the like to the aqueous dispersion, or a granule prepared by further kneading with a mineral carrier or coating a granule carrier to which a binder is previously added with this aqueous dispersion.

Examples of the thickener include natural polysaccharides such as xanthan gum, rhamsan gum, locust bean gum, carrageenan and welan gum; synthetic polymers such as sodium polyacrylate; semisynthetic polysaccharides such as carboxymethylcellulose; mineral powders such as aluminum magnesium sillicate, smectite, bentonite, hectorite and fumed silica; and others such as alumina sol. A content of the thickener is generally 0 to 10% by weight in the aqueous dispersion.

Examples of the preservative include p-hydroxybenzoate esters, salicylic acid derivatives and isothiazolin-3-one derivatives such as 1,2-benzisothiazolin-3-one, 5-chloro-2-methyl-4-isothiazolin-3-one and 2-methyl-4-isothiazolin-3-one. These may be used alone or in combination of two or more of them. In the case of using the preservative, the content thereof is generally 0.01 to 5% by weight, preferably 0.05 to 3% by weight, and even preferably about 0.1 to 1% by weight in the aqueous dispersion.

Examples of the antifreezing agent include alcohols such as propylene glycol. A content of the antifreezing agent is generally 0 to 20% by weight in the aqueous dispersion.

Examples of the specific-gravity control agent include water-soluble salts such as sodium sulfate and water-soluble organic compounds such as urea. A content of the specific-gravity control agent is generally 0 to 10% by weight in the aqueous dispersion.

When the microcapsule composition of the present invention is a granular composition, it is generally prepared with a mineral carrier, a binder, a granule carrier, or the like.

Examples of the mineral carrier used for granulation include kaolin minerals such as kaolinite, dickite, nakhlite and halloysite; serpentines such as chrysotile, lizardite, antigorite and amesite; smectites such as saponite, hectorite, sauconite and beidellite; micas such as pyrophyllite, talc, agalmatolite, muscovite, phengite, sericite and illite; silicas such as cristobalite and quartz; hydrous magnesium silicate such as attapulgite and sepiolite; calcium carbonates such as dolomite and calcium carbonate fine powder; sulfate minerals such as gypsum and chalk; and others such as zeolite, natural zeolite, tuffstone, vermiculite, laponite, pumice, diatomite, acidic white clays and activated white clays.

Examples of the binder include synthetic polymers such as acrylic polymers, vinyl polymers and polyoxyalkylene; semisynthetic polymers such as cellulose derivatives, processed starch and lignin derivatives; and natural polymers. Examples of the acrylic polymer include sodium polyacrylate and sodium polymethacrylate. Examples of the vinyl polymer include polyvinyl alcohol, polyvinylpyrrolidone and vinyl acetate copolymer. Examples of the polyoxyalkylene include polyoxyethylene and polyoxypropylene. Examples of the cellulose derivative include sodium carboxymethylcellulose, dextrin, hydroxypropylmethylcellulose, methylcellulose, methylethylcellulose and hydroxypropylcellulose. Examples of the processed starch include modified starch, carboxymethyl starch and soluble starch. Examples of the lignin derivative include sodium ligninsulfonate. Examples of the natural polymer include polysaccharides such as gum arabic, xanthan gum, tragacanth gum, guar gum, carrageenan, alginic acid and sodium alginate; and proteins such as casein, caseinlime, gelatin and collagen.

An amount of the binder used is generally 0.1 to 10% by weight, and preferably 0.5 to 5% by weight of the granular composition.

Examples of the granule carrier include pulverized minerals prepared by pulverizing and filtering natural minerals such as bentonite, attapulgite, zeolite, pumice; granules and fertilizers prepared by granulating various powders; and pulverized minerals prepared by pulverizing and filtering natural minerals limestone and silica.

EXAMPLES

The present invention will be described in detail by Formulation Examples and Test Example, but is not limited to these Examples.

Formulation Example 1

0.7 part by weight of polyvinyl alcohol (dispersion stabilizer, trade name: Gohsenol GH-17, made by Nippon Synthetic Chemical Industry Co., Ltd.) and 0.1 part by weight of sodium laurylsulfate (ionic surfactant, trade name: Emal 10 powder, made by Kao Corporation) were dissolved in 84.15 parts by weight of ion-exchanged water to give a uniform aqueous phase. To the aqueous phase was added 2.5 parts by weight of flumioxazin (volume median diameter: 2.7 µm), which is a solid compound serving as a pesticidal active component, to prepare a dispersion. To the dispersion was added 12.4 parts by weight of butyl methacrylate (radical-polymerizable monomer, made by Wako Pure Chemical Industries, Ltd.) containing 0.15 part by weight of 2,2'-azobis (2,4-dimethyl-4-methoxyvaleronitrile) (polymerization initiator, trade name: V-70, made by Wako Pure Chemical Industries, Ltd.) dissolved therein to give a mixture.

The mixture was then cooled to 5° C. and subjected to ultrasonic irradiation for 10 minutes with Ultrasonic Disruptor UD-201 (made by Tomy Seiko Co., Ltd.) at OUT PUT value of 2.

The treated mixture was gently stirred for one hour with a stirrer, and then raised to 30° C. and gently stirred for 24 hours to give microcapsules. The resultant microcapsules had an average particle diameter of 3.9 µm.

In Examples, an average particle diameter of microcapsules refers a volume median diameter, and is a value calculated by measuring a large number of particles by the laser diffraction and scattering method based on the Mie scattering theory and analyzing a resultant image.

Formulation Example 2

Microcapsules were prepared by the same operation as in Formulation Example 1, except that 1-(2-chloro-6-propylimidazo[1,2-b]pyridazin-3-ylsulfonyl)-3-(4,6-dimethoxypyrimidin-2-yl)urea was used instead of flumioxazin.

Formulation Example 3

Microcapsules were prepared by the same operation as in Formulation Example 2, except that ethyl methacrylate was used instead of butyl methacrylate.

Formulation Examples 4

0.66 g of polyvinyl alcohol (dispersion stabilizer, trade name: Gohsenol GH-17, made by Nippon Synthetic Chemical Industry Co., Ltd.) was dissolved in 22.13 g of ion-exchanged water to give an aqueous phase. To the aqueous phase was added 1-(2-chloro-6-propylimidazo[1,2-b]pyridazine-3-ylsulfonyl)-3-(4,6-dimethoxy-pyrimidin-2-yl) urea to give a dispersion.

Beside this, 0.64 g of polyvinyl alcohol (dispersion stabilizer, trade name: Gohsenol GH-17, made by Nippon Synthetic Chemical Industry Co., Ltd.) and 0.13 g of sodium laurylsulfate (ionic surfactant, trade name: Emal 10 powder, made by Kao Corporation) were dissolved in 50.8 g of ion-exchanged water to give a uniform aqueous phase. To the aqueous phase was added 16.26 g of ethyl methacrylate (radical-polymerizable monomer, made by Wako Pure Chemical Industries, Ltd.) containing 0.33 g of 2,2'-azobis(2,4-dimethyl-4-methoxyvaleronitrile) (polymerization initiator, trade name: V-70, made by Wako Pure Chemical Industries, Ltd.) dissolved therein to give a mixture. The mixture solution was cooled to 5° C. and subjected to ultrasonic irradiation for 10 minutes with Ultrasonic Disruptor UD-201 (made by TOMY SEIKO CO., LTD.) at 2 of OUT PUT value to give an emulsion. The emulsion was mixed with the dispersion prepared above to give a mixture solution.

The mixture solution was gently stirred for 30 minutes with a stirrer.

Then, the mixture solution was raised to 30° C. and gently stirred for 24 hours to give a microcapsule suspension.

To the resultant suspension were added 31.1 g of an aqueous solution containing 0.26 g of xanthan gum (thickener: Keizan S, Sansho Co., Ltd.), 0.53 g of aluminum magnesium sillicate (thickener: Beegum GR, Sansho Co., Ltd.) and 0.26 g of Proxel GXL(S) (preservative, main ingredient: 1,2-benzisothiazolin-3-one, provided by Avecia), 0.26 g of silicone antifoaming agent (FS Antifoam C, provided by Dow Corning Corporation) and 6.6 g of propylene glycol to give a microcapsule composition.

Test Example

The microcapsule composition obtained in Formulation Example 1 and water dispersible granules containing 50 parts by weight of flumioxazin that was not microencapsulated were diluted with water to give test liquids for spreading (at two concentrations, 234 ppm and 117 ppm, for each).

These test liquids were applied (224 L/ha) to pots filled with soil. Four weeks after the application, seeds of a weed (barnyard grass: *Echinochloa crus-galli*) were planted in pots to examine potencies. An effect achieved when the seed is planted in the pot immediately after the application of a test liquid of water dispersible granules is set to 1. A relative effect represent an effect relative to this base value based on a ratio of concentration of active ingredient that can achieve the same effect. Results are shown in Table 1.

TABLE 1

| | Applied concentration (ppm) | Relative effect |
|---|---|---|
| Formulation Example 1 | 234 | 85 |
| | 117 | 53 |

TABLE 1-continued

| | Applied concentration (ppm) | Relative effect |
|---|---|---|
| Water dispersible granule | 234 | 43 |
| | 117 | 40 |

INDUSTRIAL APPLICABILITY

According to the method for production of the present invention, a solid biologically active substance can be microencapsulated with an intended wall thickness and an intended particle diameter without dissolving in a solvent at ordinary temperature. Therefore, a microcapsule composition of a biologically active ingredient can be easily designed as desired and produced in order to enhance potency, reduce toxicity and impart stability.

The invention claimed is:

1. A method for producing a microcapsule, comprising: heating an aqueous dispersion comprising a dispersion stabilizer, an ionic surfactant, a solid pesticidal active compound, a polymerization initiator and a radical-polymerizable monomer subjected to ultrasonic irradiation, wherein the content of the ionic surfactant is lower than its critical micelle concentration.

2. The method for producing a microcapsule according to claim 1, comprising: preparing a mixture solution by dissolving the dispersion stabilizer and the ionic surfactant in water, dispersing the solid pesticidal active compounde in the water, and adding the polymerization initiator and the radical-polymerizable monomer to water; subjecting the mixture to ultrasonic irradiation and stifling; and heating the mixture solution.

3. The method for producing a microcapsule according to claim 1, comprising: mixing a liquid having an aqueous phase containing the dispersion stabilizer uniformly dissolved therein and the pulverized solid pesticidal active compound dispersed therein with a liquid prepared by adding the radical-polymerizable monomer containing the polymerization initiator dissolved therein to an aqueous phase containing an ionic surfactant and a dispersion stabilizer, which are uniformly dissolved therein, and subjecting the mixture to ultrasonic irradiation and stirring; and heating the mixture solution.

4. The method for producing a microcapsule according to any of claims 1 to 3, wherein the ionic surfactant is an anionic surfactant.

5. A microcapsule composition comprising a solid pesticidal active compound microencapsulated with a polymer derived from a radical-polymerizable monomer subjected to ultrasonic irradiation, a dispersion stabilizer and an ionic surfactant that are dispersed in water, wherein the content of the ionic surfactant is lower than its critical micelle concentration.

6. The microcapsule composition according to claim 5, wherein the ionic surfactant is an anionic surfactant.

* * * * *